United States Patent [19]
Patton et al.

[11] Patent Number: 5,684,212
[45] Date of Patent: Nov. 4, 1997

[54] NITRILE REMOVAL PROCESS AND ETHERIFICATION PROCESS WITH SAME

[75] Inventors: Gary R. Patton; Robert O. Dunn, both of Bartlesville, Okla.

[73] Assignee: Phillips Petroleum Company, Bartlesville, Okla.

[21] Appl. No.: 655,426

[22] Filed: May 30, 1996

[51] Int. Cl.$^6$ .................................................. C07C 41/05
[52] U.S. Cl. ........................................ 568/697; 568/699
[58] Field of Search ................................. 568/697, 699

[56] References Cited

U.S. PATENT DOCUMENTS

| 5,300,696 | 4/1994 | Luebke et al. | 568/697 |
| 5,399,787 | 3/1995 | Ozmen et al. | 568/697 |

*Primary Examiner*—Marianne M. Cintins
*Assistant Examiner*—Dwayne C. Jones
*Attorney, Agent, or Firm*—Carl D. Corvin

[57] ABSTRACT

This invention provides a process to remove nitriles. This invention also provides an improved etherification process that reduces the amount of acidic-ion-exchange-resin catalyst that is deactivated by nitriles. These processes use a water phase to remove nitriles from a hydrocarbon phase followed by a steam, or fuel gas, phase to remove the nitriles from the water phase.

17 Claims, 1 Drawing Sheet

NITRILE REMOVAL PROCESS AND ETHERIFICATION PROCESS WITH SAME

BACKGROUND

This invention relates to nitrile removal. This invention also relates to the production of compounds comprising ether linkages (—C—O—C—). In particular, this invention relates to the production of alkyl-tertiary-alkyl ethers.

Alkyl-tertiary-alkyl ethers are useful as octane improvers for liquid fuels, such as, for example, gasoline. Also, because of the low vapor pressure of alkyl-tertiary-alkyl ethers, they are particularly useful for reducing the vapor pressure of gasoline.

Federal government regulations require that some gasolines contain greater concentration levels of oxygen-containing compounds. Alkyl-tertiary-alkyl ethers have been found to be especially suitable for assisting in the compliance with these Federal regulations.

While processes for the production of alkyl-tertiary-alkyl ethers are known in the art, not all problems associated with such processes have been solved. For example, refinery-catalytic-cracker-hydrocarbon streams, which are typically used for the production of alkyl-tertiary-alkyl ethers, contain undesirable compounds, such as, for example, nitriles. Specific examples of these nitriles are acetonitrile ($CH_3CN$ also known as methyl cyanide) and propionitrile ($C_2H_5CN$ also known as ethyl cyanide). These nitriles are undesirable because they can poison an acidic-ion-exchange-resin catalyst being used in an etherification process. At levels as low as about 15 to about 30 parts per million by weight based on the total weight of a feed stream to an etherification reactor, a typical acidic-ion-exchange-resin-catalyst bed could be deactivated in as little as three months. Replacement of an acidic-ion-exchange-resin-catalyst bed could cost from about 100,000 to about 200,000 U.S. Dollars for a typical fixed-bed reactor to as high as 1,000,000 U.S. Dollars for a complex catalytic-distillation reactor. Consequently, a more efficient etherification process that reduces the amount of acidic-ion-exchange-resin catalyst that is deactivated by such nitriles would be of great value both economically and technologically.

SUMMARY

It is an object of this invention to provide a nitrile removal process.

It is another object of this invention to provide an improved etherification process that resists deactivation, by nitriles, of its acidic-ion-exchange-resin catalyst.

In accordance with this invention a nitrile removal process is provided. This process comprises (or optionally consists essentially of):

(a) contacting a First Isoolefin Stream, which comprises isoolefins, nitriles, and nonreactive compounds, with a First Water Stream, which comprises water, in a first contacting means under conditions that produce a Second Isoolefin Stream and a Second Water Stream from said First Isoolefin Stream and said First Water Stream, where said Second Isoolefin Stream comprises said isoolefins and said nonreactive compounds, and where said Second Water Stream comprises said water and said nitriles, and where said Second Isoolefin Stream is lean in said nitriles when compared with said First Isoolefin Stream, and where said Second Water Stream is rich in said nitriles when compared with said First Water Stream;

(b) contacting said Second Water Stream with a First Steam Stream, or a First Fuel Gas Stream, in a contacting zone under conditions that produce a First Nitrile Steam, from said Second Water Stream and said First Steam Stream, or said First Fuel Gas Stream, where said First Nitrile Stream comprises said nitriles.

In accordance with this invention, an improved etherification process that resists deactivation, by nitriles, of its acidic-ion-exchange-resin catalyst, is provided. This process comprises (or optionally consists essentially of):

(a) contacting a First Isoolefin Stream, which comprises isoolefins, nitriles, and nonreactive compounds, with a First Water Stream, which comprises water, in a first contacting means under conditions that produce a Second Isoolefin Stream and a Second Water Stream from said First Isoolefin Stream and said First Water Stream, where said Second Isoolefin Stream comprises said isoolefins and said nonreactive compounds, and where said Second Water Stream comprises said water and said nitriles, and where said Second Isoolefin Stream is lean in said nitriles when compared with said First Isoolefin Stream, and where said Second Water Stream is rich in said nitriles when compared with said First Water Stream;

(b) contacting said Second Isoolefin Stream with a First Alcohol Stream, which comprises alcohols, in an Isoolefin/Alcohol contacting zone where said Second Isoolefin Stream can come into contact with said First Alcohol Stream, to form a First Isoolefin/Alcohol Stream that comprises said isoolefins, said nonreactive compounds, and said alcohols;

(c) contacting said First Isoolefin/Alcohol Stream with an acidic-ion-exchange-resin catalyst, in a second contacting zone under conditions that produce a First Ether Stream from said First Isoolefin/Alcohol Stream, where said First Ether Stream comprises unreacted isoolefins, unreacted alcohols, said nonreactive compounds, and ethers;

(d) separating said First Ether Stream in a first separating zone under conditions that produce a Second Isoolefin/Alcohol Stream and a Second Ether Stream from said First Ether Stream, where said Second Isoolefin/Alcohol Stream comprises said unreacted isoolefins, said unreacted alcohols, and said nonreactive compounds, and said Second Ether Stream comprises said ethers, and where said Second Isoolefin/Alcohol Stream is lean in said ethers and said Second Ether Stream is rich in said ethers;

(e) contacting said Second Isoolefin/Alcohol Stream with a Third Water Stream in a third contacting zone under conditions that produce a First Alcohol/Water Stream and a Third Isoolefin Stream from said Second Isoolefin/Alcohol Stream and said Third Water Stream, where said Third Isoolefin Stream comprises said unreacted isoolefins and said nonreactive compounds, and where said First Alcohol/Water Stream comprises said unreacted alcohols and said water;

(f) separating said First Alcohol/Water Stream in a second separating zone where said First Alcohol/Water Stream is separated under conditions that produce said Third Water Stream and said First Alcohol Stream from said First Alcohol/Water Stream, where said First Alcohol Stream comprises said unreacted alcohols, and said Third Water Stream comprises water, and where said First Alcohol Stream is rich in said alcohols and said Third Water Stream is lean in said alcohols;

(g) contacting said Second Water Stream with a First Steam Stream, or a First Fuel Gas Stream, in a fourth contacting zone under conditions that produce said First Water Stream and a First Nitrile Stream, from said Second Water Stream and said First Steam Stream, or said First Fuel Gas Stream, where said First Water Stream comprises said water and said First Nitrile Stream comprises said nitriles, and where said First Water Stream is lean in said nitriles and said First Nitrile Stream is rich in said nitriles.

Other objects of this invention and their advantages will become apparent from the following.

BRIEF DESCRIPTION OF THE FIGURE

The FIGURE is a diagrammatic representation of a preferred embodiment of an Etherification Structure that is useful in performing a preferred embodiment of the process of this invention. The FIGURE will be described in more detail herein.

DETAILED DESCRIPTION OF THE INVENTION

Figure 1:
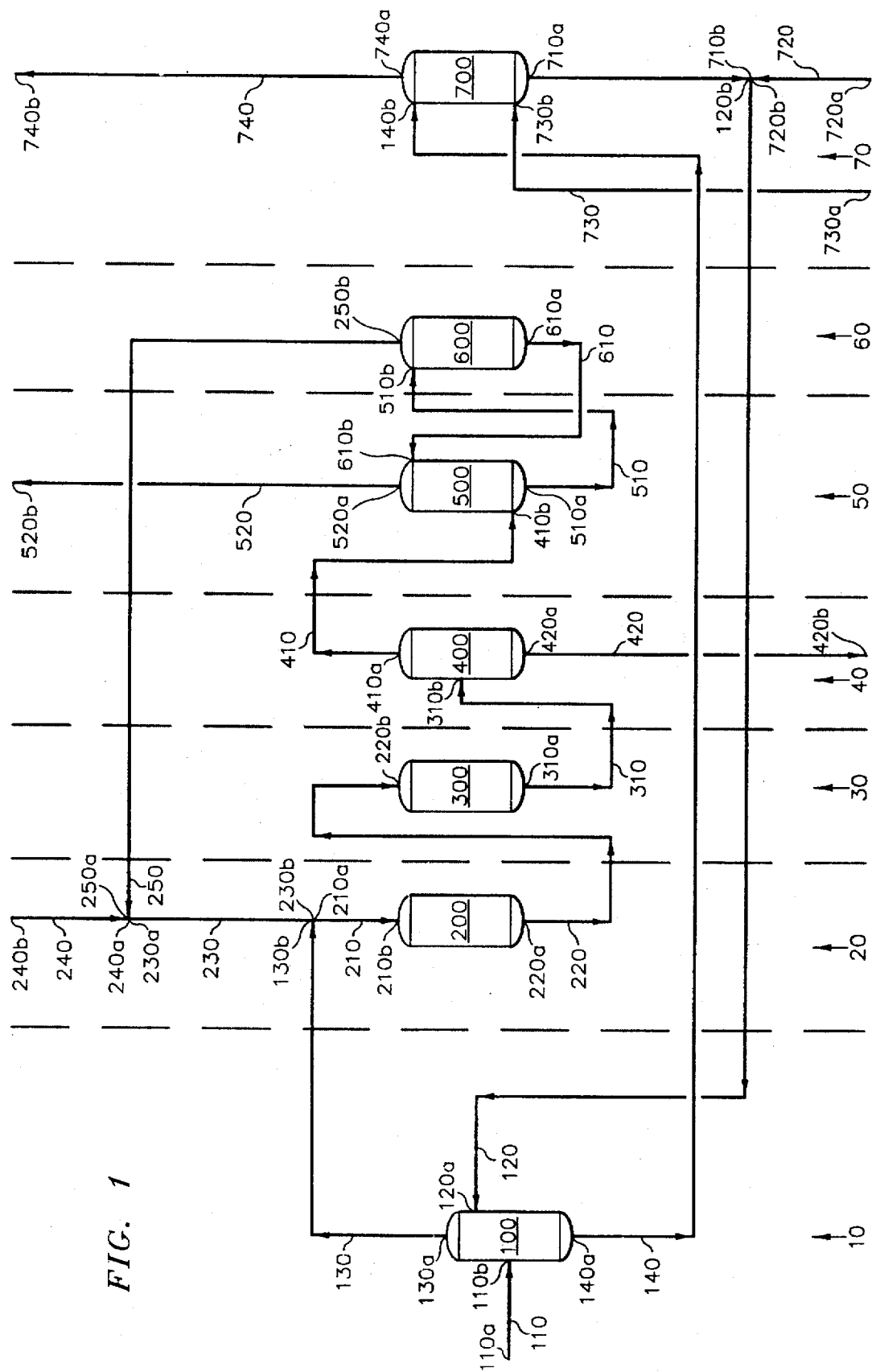

Alkyl-tertiary-alkyl ethers can be produced by reacting primary alcohols, or secondary alcohols, with isoolefin compounds, in the presence of an acidic-ion-exchange-resin catalyst. Common etherification reactions involve reacting methanol with various isoalkenes, such as, for example:

2-methyl-1-propene (($CH_3)_2C:CH_2$ also known as isobutylene);

2-methyl-1-butene ($H_2C:C(CH_3)CH_2CH_3$); or 2-methyl-2-butene ($H_3CCH:C(CH_3)_2$ also known as β-isoamylene);

to form alkyl-tertiary-alkyl ethers.

The isoolefins useful in this invention are generally alkenes having from 4 to about 16 carbon atoms per molecule. Suitable examples of these isoolefins are isobutylene, isoamylene, isohexylene, isoheptylene, isooctylene, isononylene, isodecylene, isoundecylene, isododecylene, isotridecylene, isotetradecylene, isopentadecylene, and isohexadecylene. Mixtures of two or more of these isoolefins can also be used in this invention.

The alcohols useful in this invention are generally primary alcohols, or secondary alcohols, having from 1 to about 12 carbon atoms per molecule. Suitable examples of these alcohols are methanol, ethanol, propanol, isopropanol, butanol, secondary butanol, pentanol, hexanol, ethylene glycol, propylene glycol, butylene glycol, and glycerol. Mixtures of two or more of these alcohols can also be used in this invention. Polyethylene glycols can also be used in this invention in place of, or in conjunction with, the above-identified types of alcohols.

Currently, the preferred isoolefins are isobutylene and the isoamylenes. This is because they can react with methanol and ethanol, which is the currently preferred alcohols, to produce, respectively, methyl-tertiary-butyl ether, methyl-tertiary-amyl ether, and ethyl-tertiary-butyl-ether.

Any suitable molar ratio of alcohol to isoolefin can be used in this invention. In general, the molar ratio of alcohol to isoolefin in the feed stream to the ether-production vessel can be in the range of about 0.5:1 to about 4:1. It is preferable if said ratio is from about 0.8:1 to about 1.2:1 and it is most preferable if said ratio is 1:1.

The acidic-ion-exchange-resin catalysts useful in this invention are generally sulfonated coals and sulfonated resins. These catalysts can be used separately or together in the same etherification reactor.

The sulfonated coals useful in this invention are generally high molecular weight carbonaceous materials that contain at least one $SO_3H$ group. Suitable examples of such sulfonated coals are available under the designations "Zeo-Karb H"™, "Nalcite X"™, and "Nalcite AX"™. These sulfonated coals can be obtained from various commercial sources. Sulfonated coals are generally produced by the treatment of bituminous coals with sulfuric acid. They are often marketed as water softeners or base exchangers. These materials are usually available in a neutralized form and as such must be activated to the acidic form by treatment with a strong mineral acid. Usually water is then used to remove any remaining sodium and chloride ions prior to use.

The sulfonated resins useful in this invention are generally hydrocarbon polymers that contain at least one $SO_3H$ group. Sulfonated resins are presently preferred as the acidic-ion-exchange-resin catalysts used in this invention. Suitable examples include, but are not limited to, the reaction products of phenol formaldehyde resins with sulfuric acid. Commercial examples of these resins are available under the designations "Amberlite IR-1"™, "Amberlite IR-100"™ and "Nalcite MX"™. Also useful are the sulfonated resinous polymers of coumarone-indene with cyclopentadiene and furfural, and sulfonated polymers of cyclopentadiene with furfural.

Currently, the most preferred acidic-ion-exchange-resin catalysts are the sulfonated polystyrene resins. Suitable examples of these sulfonated polystyrene resins include, but are not limited to, a divinylbenzene crosslinked polystyrene matrix having from about 0.5 to 20 weight percent, preferably from about 4 to about 16 weight percent, of copolymerized divinylbenzene therein to which are functionable sulfonic acid groups, or groups ionizable to functional sulfonic acid groups. These resins are commercially available under the designation "Dowex 50"™, "Nalcite HCR"™, and "Amberlyst 15"™. These resins when commercially obtained have solvent contents of about 50 weight percent. This solvent can either be removed before use or the resin can be used as-is.

The resin particle size can be any suitable size, however, particle sizes from about 10 to about 50 mesh (U.S. Sieve Series) are currently preferred.

The isoolefins used in this invention are usually obtained from a refinery-catalytic-cracker-hydrocarbon stream. Such streams usually comprise isoolefins, nitriles, and other non-reactive compounds. The nonreactive compounds are usually hydrocarbons that do not react, or react very slowly, when they come into contact with an acidic-ion-exchange-resin catalyst. Typical examples of such nonreactive compounds include, but are not limited to, alkanes and straight chain olefins. The nonreactive compounds are also useful as diluents in this invention.

The temperature of the steam used in this invention can be in the range of about 100° C. to about 300° C. However, it is more preferred if the temperature of the steam is in the range of 125° C. to 200° C. The pressure, under which the steam is used in this invention, can be in the range of about 10 psig to about 200 psig. However, it is more preferred if the pressure is in the range of 20 psig to 100 psig.

The fuel gas used in this invention can be any composition that can be burned in a furnace for the generation of heat or used in an engine for the generation of power. The fuel gas can be, for example, a distillated fraction of petroleum, a residuum from refinery operations, a crude petroleum, or a mixture of two or more of these. Typically, the temperature of the fuel gas can be in the range of about 50° C. to about 250° C. However, it is more preferred if the temperature of the fuel gas is in the range of 75° C. to 175° C. The pressure, under which the fuel is used in this invention, can be in the range of about 10 psig to about 200 psig. However, it is more preferred if the pressure is in the range of 75 psig to 175 psig.

Additional information concerning these types of processes can be found in U.S. Pat. No. 5,237,109 (the disclosure of which is hereby incorporated by reference).

In accordance with this invention, a First Isoolefin Stream, which comprises isoolefins, nitriles, and nonreactive compounds, is contacted with a First Water Stream, which comprises water, in a first contacting means that provides a first contacting zone where said First Isoolefin Stream can come into contact with said First Water Stream. An example of such first contacting means is a wash column. This is the first nitrile-removal stage. This contacting takes place under conditions that produce a Second Isoolefin Stream and a Second Water Stream from said First Isoolefin Stream and said First Water Stream, where said Second Isoolefin Stream comprises said isoolefins and said nonreactive compounds, and where said Second Water Stream comprises said water and said nitriles, and where said Second Isoolefin Stream is lean in said nitriles when compared with said First Isoolefin Stream, and where said Second Water Stream is rich in said nitriles when compared with said First Water Stream. In general, the temperature, in said first contacting means, should be from about 10° C. to about 100° C. and the pressure should be from about 15 psig to about 150 psig. Currently, it is preferred if the temperature is from 20° C. to 50° C. and if the pressure is from 25 psig to 125 psig.

Said Second Isoolefin Stream is then contacted with a First Alcohol Stream, which comprises alcohols, in an Isoolefin/Alcohol contacting means that provides an Isoolefin/Alcohol contacting zone where said Second Isoolefin Stream can come into contact with said First Alcohol Stream, to form a First Isoolefin/Alcohol Stream that comprises said isoolefins, said nonreactive compounds, and said alcohols: Examples of said Isoolefin/Alcohol-contacting means are conduits and/or connecting ends.

Said First Isoolefin/Alcohol Stream is contacted with an acidic-ion-exchange-resin catalyst, in a second contacting means that provides a second contacting zone where said First Isoolefin/Alcohol Stream can come into contact with an acidic-ion-exchange-resin catalyst and thereby produce ethers. An example of said second contacting means is a reactor. Further information concerning reactors can be found in the *Encyclopedia of Chemical Processing and Design* vol.46, pages 245–350 (1994). This is the ether-production step. This contacting takes place under conditions that produce a First Ether Stream from said First Isoolefin/Alcohol Stream, where said First Ether Stream comprises unreacted isoolefins, unreacted alcohols, said nonreactive compounds, and said ethers. In general, the temperature, inside said second contacting means, should be from about 0° C. to about 150° C. and the pressure should be from about 30 psig to about 300 psig. Currently, it is preferred if the temperature is from 25° C. to 75° C. and if the pressure is from 25 psig to 125 psig. Generally, these etherification reactions are conducted with most of the reactants in the liquid phase. When such etherification reactions are performed with most of the reactants in the liquid phase, the liquid hourly space velocity (LHSV) of the feed to the etherification vessel should be from about 1/hour to about 20/hour. Preferably the LHSV is from about 2/hour to about 10/hour and most preferably the LHSV is from 3/hour to 5/hour.

Said First Ether Stream can optionally be contacted with another acidic-ion-exchange-resin catalyst in a separate contacting means that provides a separate contacting zone where said First Ether Stream can come into contact with an acidic-ion-exchange-resin catalyst, which can be the same as, or different from, the acidic-ion-exchange-resin catalyst used in said second contacting means. Said separate contacting means can be the same as, or different from, said second contacting means. In general, the temperature and pressure conditions inside said separate contacting means can be the same as, or different from, the conditions used in said second contacting means.

Said First Ether Stream is separated in a first separating means that provides a first separating zone where said First Ether Stream is separated into two streams where one stream is rich in said ethers and the other is lean in said ethers. An example of said first separating means is a fractionator. Further information concerning fractionators can be found in the *Encyclopedia of Chemical Processing and Design* vol. 16, pages 42–133 (1982). This is the ether-separation step. This separating takes place under conditions that produce a Second Isoolefin/Alcohol Stream and a Second Ether Stream from said First Ether Stream, where said Second Isoolefin/Alcohol Stream comprises said unreacted isoolefins, said unreacted alcohols, and said nonreactive compounds, and said Second Ether Stream comprises said ethers, and where said Second Second Ether Stream is lean in said ethers and said Second Isoolefin Stream is rich in said ethers. In general, the temperature, inside said first separating means, should be from about 10° C. to about 250° C. and the pressure should be from about 0 psig to about 300 psig. Currently, it is preferred if the temperature is from 20° C. to 200° C. and if the pressure is from 100 psig to 200 psig.

Said Second Ether Stream exits said first separating means and enters an ether-collection point.

Said Second Isoolefin/Alcohol Stream is contacted with a Third Water Stream in a third contacting means that provides a third contacting zone where said Second Isoolefin/Alcohol Stream can come into contact with said Third Water Stream. An example of said third contacting means is an extractor. Further information concerning extractors can be found in the *Encyclopedia of Chemical Processing and Design* vol. 16, pages 42–133 (1982). This is the isoolefin/nonreactive-compound-extraction step. This contacting takes place under conditions that produce a First Alcohol/Water Stream and a Third Isoolefin Stream from said Second Isoolefin/Alcohol Stream and said Third Water Stream, where said Third Isoolefin Stream comprises said unreacted isoolefins and said nonreactive compounds, and where said First Alcohol/Water Stream comprises said unreacted alcohols and said water. In general, the temperature, inside said third contacting means, should be from about 10° C. to about 100° C. and the pressure should be from about 15 psig to about 150 psig. Currently, it is preferred if the temperature is from 25° C. to 65° C. and if the pressure is from 25 psig to 65 psig.

Said Third Isoolefin Stream exits said third contacting means and enters said nonreactive-compound-collection point.

Said First Alcohol/Water Stream is separated in a second separating means that provides a second separating zone where said First Alcohol/Water Stream is separated into two streams where one stream is rich in said alcohols and the other is lean in said alcohols. An example of said second separating means is a fractionator. This is the alcohol-removal step. This contacting takes place under conditions that produce said Third Water Stream and said First Alcohol Stream from said First Alcohol/Water Stream, where said First Alcohol Stream comprises said unreacted alcohols, and said Third Water Stream comprises water, and where said First Alcohol Stream is rich in said alcohols and said Third Water Stream is lean in said alcohols. In general, the temperature inside said second separating means should be from about 50° C. to about 150° C. and the pressure should be from about 10 psig to about 100 psig. Currently, the preferred temperatures are from 75° C. to 125° C. and the preferred pressures are from 15 psig to 45 psig.

Said Second Water Stream is contacted with a First Steam Stream, or First Fuel Gas Stream in a fourth contacting means that provides a fourth contacting zone where said Second Water Stream can come into contact with said First Steam Stream, or said First Fuel Gas Stream. An example of said fourth contacting means is a extractor. This is the second nitrile-removal step. This contacting takes place under conditions that produce said First Water Stream and a First Nitrile Stream, from said Second Water Stream and said First Steam Stream, or said First Fuel Gas Stream, where said First Water Stream comprises said water and said First Nitrile Stream comprises said nitriles, and where said First Water Stream is lean in said nitriles and said First Nitrile Stream is rich in said nitriles. In general, the temperature inside said fourth contacting means should be from about 20° C. to about 150° C. and the pressure should be from about 50 psig to about 400 psig. Currently, the preferred temperatures are from 50° C. to 70° C. and the preferred pressures are from 100 psig to 200 psig.

Said First Water Stream exits said fourth contacting means and enters said first contacting means.

Said First Nitrile Stream exits said fourth contacting means and enters a nitrile-collection point.

The FIGURE is a diagrammatic representation of a preferred embodiment of an Etherification Structure that is useful in performing a preferred embodiment of the process of the invention. The following is a more detailed discussion of said FIGURE.

Said Etherification Structure 1 comprises a First Section 10, a Second Section 20, a Third Section 30, a Fourth Section 40, a Fifth Section 50, a Sixth Section 60, and a Seventh Section 70.

Said First Section, which is the first nitrile-removal stage, comprises a First Vessel 100, a First Conduit 110, a Second Conduit 120, a Third Conduit 130, and a Fourth Conduit 140. Said First Conduit 110 has Connecting Ends 110a and 110b. Said Second Conduit 120 has Connecting Ends 120a and 120b. Said Third Cconduit 130 has Connecting Ends 130a and 130b. Said Fourth Conduit 140 has Connecting Ends 140a and 140b.

Said Second Section, which is the first ether-production stage, comprises a Second Vessel 200, a Fifth Conduit 210, a Sixth Conduit 220, a Seventh Conduit 230, an Eighth Conduit 240, and a Ninth Conduit 250. Said Fifth Conduit 210 has Connecting Ends 210a and 210b. Said Sixth Conduit 220 has Connecting Ends 220a and 220b. Said Seventh Conduit 230 has Connecting Ends 230a and 230b. Said Eighth Conduit 240 has Connecting Ends 240a and 240b. Said Ninth Conduit 250 has Connecting Ends 250a and 250b.

Said Third Section, which is the second ether-production stage, comprises a Third Vessel 300, and a Tenth Conduit 310. Said Tenth Conduit 310 has Connecting Ends 310a and 310b.

Said Fourth Section, which is the ether-removal stage, comprises a Fourth Vessel 400, an Eleventh Conduit 410, and a Twelfth Conduit 420. Said Eleventh Conduit 410 has Connecting Ends 410a and 410b. Said Twelfth Conduit 420 has Connecting Ends 420a and 420b.

Said Fifth Section, which is the isoolefin/nonreactive-compound-removal stage, comprises a Fifth Vessel 500, a Thirteenth Conduit 510, and a Fourteenth Conduit 520. Said Thirteenth Conduit 510 has Connecting Ends 510a and 510b. Said Fourteenth Conduit 520 has Connecting Ends 520a and 520b.

Said Sixth Section, which is the alcohol removal stage, comprises a Sixth Vessel 600 and a Fifteenth Conduit 610. Said Fifteenth Conduit 610 has Connecting Ends 610a and 610b.

Said Seventh Section, which is the second nitrile-removal stage, comprises a Seventh Vessel 700, a Sixteenth Conduit 710, a Seventeenth Conduit 720, an Eighteenth Conduit 730, and a Nineteenth Conduit 740. Said Sixteenth Conduit 710 has Connecting Ends 710a and 710b. Said Seventeenth Conduit 720 has Connecting Ends 720a and 720b. Said Eighteenth Conduit 730 has Connecting Ends 730a and 730b. Said Nineteenth Conduit 740 has Connecting Ends 740a and 740b.

Said Connecting End 110a is connected in fluid-flow communication with an isoolefin source, which is not depicted. Said Connecting End 110b is connected in fluid-flow communication with said First Vessel 100. Said Connecting End 120a is connected in fluid-flow communication with said First Vessel 100. Said Connecting End 120b is connected in fluid-flow communication with said Connecting Ends 710b and 720b. Said Connecting End 130a is connected in fluid-flow communication with said First Vessel 100. Said Connecting End 130b is connected in fluid-flow communication with said Connecting End 210a. Said Connecting End 140a is connected in fluid-flow communication with said First Vessel 100. Said Connecting End 140b is connected in fluid-flow communication with said Seventh Vessel 700.

Said Connecting End 210a is connected in fluid-flow communication with said Connecting Ends 130b and 230b. Said Connecting End 210b is connected in fluid-flow communication with said Second Vessel 200. Said Connecting End 220a is connected in fluid-flow communication with said Second Vessel 200. Said Connecting End 220b is connected in fluid-flow communication with said Third Vessel 300. Said Connecting End 230a is connected in fluid-flow communication with said Connecting Ends 240a and 250a. Said Connecting End 230b is connected in fluid-flow communication with said Connecting End 210a. Said Connecting End 240a is connected in fluid-flow communication with said Connecting End 230a. Said Connecting End 240b is connected in fluid-flow communication with an alcohol source, which is not depicted. Said Connecting End 250a is connected in fluid-flow communication with said Connecting End 230a. Said Connecting End 250b is connected in fluid-flow communication with said Sixth Vessel 600.

Said Connecting End 310a is connected in fluid-flow communication with said Third Vessel 300. Said Connecting End 310b is connected in fluid-flow communication with said Fourth Vessel 400.

Said Connecting End 410a is connected in fluid-flow communication with said Fourth Vessel 400. Said Connecting End 410b is connected in fluid-flow communication with said Fifth Vessel 500. Said Connecting End 420a is connected in fluid-flow communication with said Fourth Vessel 400. Said Connecting End 420b is connected in fluid-flow communication with an ether-collection point, which is not depicted.

Said Connecting End 510a is connected in fluid-flow communication with said Fifth Vessel 500. Said Connecting End 510b is connected in fluid-flow communication with said Sixth Vessel 600. Said Connecting End 520a is connected in fluid-flow communication with said Fifth Vessel 500. Said Connecting End 520b is connected in fluid-flow communication with an isoolefin/nonreactive-compound-collection point, which is not depicted.

Said Connecting End 610a is connected in fluid-flow communication with said Sixth Vessel 600. Said Connecting End 610b is connected in fluid-flow communication with said Fifth Vessel 500.

Said Connecting End 710a is connected in fluid-flow communication with said Seventh Vessel 700. Said Connecting End 710b is connected in fluid-flow communication with said Connecting End 120b. Said Connecting End 720a is connected in fluid-flow communication with a water source, which is not depicted. Said Connecting End 720b is connected in fluid-flow communication with said Connecting End 120b. Said Connecting End 730a is connected in fluid-flow communication with a steam, or fuel-gas, source, which is not depicted. Said Connecting End 730b is connected in fluid-flow communication with said Seventh Vessel 700. Said Connecting End 740a is connected in fluid-flow communication with said Seventh Vessel 700. Said Connecting End 740b is connected in fluid-flow communication with a nitrile-collection point, which is not depicted.

A First Stream, which comprises isoolefins, nitriles, and nonreactive compounds, originates from said isoolefin source. Said First Stream exits said isoolefin source through said Connecting End 110a and enters said Conduit 110. Said First Stream exits said First Conduit 110 through said Connecting End 110b and enters said First Vessel 100 which is said first contacting means.

A Second Stream, which comprises water, exits said Conduit 120 through said Connecting End 120a and enters said First Vessel 100.

Said First Vessel 100 is a contacting means that provides a contacting zone where said First Stream can come into contact with said Second Stream. An example of said contacting means is a wash column. This contacting takes place under conditions that produce a Third Stream and a Fourth Stream from said First Stream and said Second Stream, where said Third Stream comprises said isoolefins and said nonreactive compounds, and where said Fourth Stream comprises said water and said nitriles, and where said Third Stream is lean in said nitriles when compared with said First Stream, and where said Fourth Stream is rich in said nitriles when compared with said Second Stream.

Said Third Stream exits from said First Vessel 100 through said Connecting End 130a and enters said Conduit 130. Said Third Stream exits said Conduit 130 through Connecting End 130b and enters said Connecting End 210a.

Said Fourth Stream exits said First Vessel 100 through said Connecting End 140a and enters said Conduit 140. Said Fourth Stream exits said Conduit 140 through Connecting End 140b and enters said Seventh Vessel 700.

An Eighth Stream, which comprises make-up alcohols, originates from said alcohol source. Said Eighth Stream exits said alcohol source through said Connecting End 240b and enters said Conduit 240. Said Eighth Stream exits said Conduit 240 through said Connecting End 240a and enters said Connecting End 230a.

A Ninth Stream, which comprises recycled alcohols, exits said Conduit 250 through said Connecting End 250a and enters said Connecting End 230a.

Said Eighth Stream and said Ninth Stream combine in said Connecting End 230a to form a Seventh Stream, which comprises said alcohols. Said Seventh Stream exits said Connecting End 230a and enters said Conduit 230. Said Seventh Stream exits said Conduit 230 through said Connecting End 230b and enters said Connecting End 210a.

Said Seventh Stream and said Third Stream combine in said Connecting End 210a to form a Fifth Stream, which comprises said isoolefins, said alcohols, and said nonreactive compounds, and enters said Conduit 210. Said Fifth Stream exits said Conduit 210 through said Connecting End 210b and enters said Second Vessel 200 which is said second contacting means.

Said Conduits 130, 210, 230, and their Connecting Ends form said Isoolefin/Alcohol contacting means.

Said Second Vessel 200 is a contacting means that provides a contacting zone where said Fifth Stream can come into contact with an acidic-ion-exchange-resin catalyst and thereby produce ethers. An example of said contacting means is a reactor. This contacting takes place under conditions that produce a Sixth Stream from said Fifth Stream, where said Sixth Stream comprises unreacted isoolefins, unreacted alcohols, said nonreactive compounds, and said ethers.

Said Sixth Stream exits said Second Vessel 200 through Connecting End 220a and enters said Conduit 220. Said Sixth Stream exits said Conduit 220 through Connecting End 220b and enters said Third Vessel 300 which is said separate contacting means.

Said Third Vessel 300 is a contacting means that provides a contacting zone where said Sixth Stream can come into contact with an acidic-ion-exchange-resin catalyst, which can be the same as, or different from, the acidic-ion-exchange-resin catalyst used in said Second Vessel 200. An example of said contacting means is a reactor, which can be the same as, or different from, said Second Vessel 200. This contacting takes place under conditions that produce a Tenth Stream from said Sixth Stream, where said Tenth Stream comprises unreacted isoolefins, unreacted alcohols, said nonreactive compounds, and ethers, and where said Tenth Stream is richer in said ethers than said Sixth Stream. The temperatures and pressures in said Second Vessel 200 and said Third Vessel 300 can be the same, or different, depending on, among other things, desired products.

Said Tenth Stream exits said Third Vessel through said Connecting End 310a and enters said Conduit 310. Said Tenth Stream exits said Conduit 310 through said Connecting End 310b and enters said Fourth Vessel 400 which is said first separating means.

Said Fourth Vessel 400 is a separating means that provides a separating zone where said Tenth Stream is separated into two streams where one stream is rich in said ethers and the other is lean in said ethers. An example of said contacting means is a fractionator. This contacting takes place under conditions that produce an Eleventh Stream and a Twelfth Stream from said Tenth Stream, where said Eleventh Stream comprises said unreacted isoolefins, said unreacted alcohols, and said nonreactive compounds, and said Twelfth Stream comprises said ethers, and where said Eleventh Stream is lean in said ethers and said Twelfth Stream is rich in said ethers.

Said Eleventh Stream exits said Fourth Vessel 400 through said Connecting End 410a and enters said Conduit 410. Said Eleventh Stream exits said Conduit 410 through said Connecting End 410b and enters said Fifth Vessel 500 which is said third contacting means.

Said Twelfth Stream exits said Fourth Vessel 400 through said Connecting End 420a and enters said Conduit 420. Said Twelfth Stream exits said Conduit 420 through said Connecting End 420b and enters said ether-collection point.

Said Fifth Vessel 500 is a contacting means that provides a contacting zone where said Eleventh Stream can come into contact with a Fifteenth Stream, which comprises water. An example of said contacting means is an extractor. This contacting takes place under conditions that produce a Thirteenth Stream and a Fourteenth Stream from said Eleventh Stream and said Fifteenth Stream, where said Fourteenth Stream comprises said unreacted isoolefins and said nonreactive compounds, and where said Thirteenth Stream comprises said unreacted alcohols and said water.

Said Thirteenth Stream exits said Fifth Vessel 500 through said Connecting End 510a and enters said Conduit 510. Said Thirteenth Stream exits said Conduit 510 through said Connecting End 510b and enters said Sixth Vessel 600 which is said second separating means.

Said Fourteenth Stream exits said Fifth Vessel 500 through said Connecting End 520a and enters said Conduit 520. Said Fourteenth Stream exits said Conduit 520 through said Connecting End 520b and enters said nonreactive-compound-collection point.

Said Sixth Vessel 600 is a second separating means that provides a second separating zone where said Thirteenth Stream is separated into two streams where one stream is rich in said alcohols and the other is lean in said alcohols. An example of said contacting means is a fractionator. This contacting takes place under conditions that produce said Fifteenth Stream and said Ninth Stream from said Thirteenth Stream, where said Fifteenth Stream comprises said water, and said Ninth Stream comprises said alcohols, and where said Fifteenth Stream is lean in said alcohols and said Ninth Stream is rich in said alcohols.

Said Fifteenth Stream exits said Sixth Vessel 600 through said Connecting End 610a and enters said Conduit 610. Said Fifteenth Stream exits said Conduit 610 through said Connecting End 610b and enters said Fifth Vessel 500.

Said Sixteenth Stream, which comprises water, exits said Seventh Vessel 700 through said Connecting End 710a and enters said Conduit 710. Said Sixteenth Stream exits said Conduit 710 through said Connecting End 710b and enters said Connecting End 120b.

Said Seventeenth Stream exits said water source through said Connecting End 720a and enters said Conduit 720. Said Seventeenth Stream exits said Conduit 720 through said Connecting End 720b and enters said Connecting End 120b.

Said Sixteenth Stream and said Seventeenth Stream combine in said Connecting End 120b to form said Second Stream, which comprises said water. Said Second Stream exits said Connecting End 120b and enters said Conduit 120. Said Second Stream exits said Conduit 120 through said Connecting End 120a and enters said First Vessel 100.

Said Eighteenth Stream, which comprises steam, or fuel-gas, originates from said steam, or said fuel gas, source. Said Eighteenth Stream exits said steam, or said fuel gas, source through said Connecting End 730a and enters said Conduit 730. Said Eighteenth Stream exits said Conduit 730 through said Connecting End 730b and enters said Seventh Vessel 700, which is said fourth contacting means.

Said Seventh Vessel 700 is a contacting means that provides a contacting zone where said Eighteenth Stream can come into contact with said Fourth Stream. An example of said contacting means is a extractor. This contacting takes place under conditions that produce said Sixteenth Stream and said Nineteenth Stream from said Eighteenth Stream, where said Sixteenth Stream comprises said water.

Said Nineteenth Stream exits said Seventh Vessel 700 through said Connecting End 740a and enters said Conduit 740. Said Nineteenth Stream exits said Conduit 740 through said Connecting End 740b and enters said nitrile-collection point.

CALCULATED EXAMPLE

This calculated example is provide to further assist those skilled in the art with understanding this invention.

A material balance based on certain streams in the FIGURE is tabulated in Table One.

TABLE I

|  | Conduit 110 | Conduit 130 | Conduit 720 | Conduit 730 | Conduit 740 |
| --- | --- | --- | --- | --- | --- |
| Temp °F. | 100.2589 | 100.0000 | 100.0000 | 281.0987 | 100.0000 |
| Pressure psia | 100.0000 | 100.0000 | 15.0000 | 50.0000 | 15.0000 |
| Enth MMBtu/hr | −50.296 | −50.043 | −6.995 | −65.899 | −62.829 |
| Vapor Mole Fraction | 0.00000 | 0.00000 | 0.00000 | 0.00100000 | 0.000174768 |
| Total lb mol/hr | 941.0789 | 939.0842 | 57.1139 | 553.2468 | 512.8185 |
| Total lb/hr | 66806.9219 | 66778.3125 | 1028.9072 | 9966.7412 | 9245.7461 |
| Total std L gpm | 209.1954 | 209.1479 | 2.0571 | 19.9265 | 18.4948 |
| Total std V scfh | 357119.31 | 356362.41 | 21673.51 | 209945.34 | 194603.66 |
| Isoamylenes[1] | 15098.385 | 15099.998 | 0.0000 | 0.0000 | 1.6116 |
| Water[1] | 38.8572 | 0.0000 | 1028.9072 | 9966.7412 | 9235.5020 |
| I-Pentane[1] | 14999.2354 | 15000.0000 | 0.0000 | 0.0000 | 0.7656 |
| N-Pentane[1] | 24998.4980 | 24999.9980 | 0.0000 | 0.0000 | 1.5001 |
| 1-Pentane[1] | 10997.9023 | 11000.0000 | 0.0000 | 0.0000 | 2.0974 |
| Acetonitrile[1] | 0.0000 | 0.0000 | 0.0000 | 0.0000 | 0.0000 |
| 1,3-Butadiene[1] | 673.6742 | 674.9437 | 0.0000 | 0.0000 | 1.2695 |
| Propionitrile[1] | 0.3743 | 3.3747 | 0.0000 | 0.0000 | 3.0003 |

[1]Flowrates in lb/hr

The calculated results in Table One show that a substantial amount of the nitrile compounds can be removed from the etherification structure before they can come into contact with an acidic-ion-exchange-resin catalyst.

While this invention has been described in considerable detail with certain preferred embodiments stated, the appended claims should not be construed as limited to only the preferred embodiments, but should be considered in light of the entire specification.

That which is claimed:

1. An etherification process that resists deactivation, by nitriles, of its acidic-ion-exchange-resin catalyst, said process comprising:

(a) contacting a First Isoolefin Stream, which comprises isoolefins, nitriles, and nonreactive compounds, with a First Water Stream, which comprises water, in a first contacting means under conditions that produce a Second Isoolefin Stream and a Second Water Stream from said First Isoolefin Stream and said First Water Stream, where said Second Isoolefin Stream comprises said isoolefins and said nonreactive compounds, and where said Second Water Stream comprises said water and said nitriles, and where said Second Isoolefin Stream is lean in said nitriles when compared with said First Isoolefin Stream, and where said Second Water Stream is rich in said nitriles when compared with said First Water Stream;

(b) contacting said Second Isoolefin Stream with a First Alcohol Stream, which comprises alcohols, in an Isoolefin/Alcohol contacting zone where said Second Isoolefin Stream can come into contact with said First Alcohol Stream, to form a First Isoolefin/Alcohol Stream that comprises said isoolefins, said nonreactive compounds, and said alcohols;

(c) contacting said First Isoolefin/Alcohol Stream with an acidic-ion-exchange-resin catalyst, in a second contacting zone under conditions that produce a First Ether Stream from said First Isoolefin/Alcohol Stream, where said First Ether Stream comprises unreacted isoolefins, unreacted alcohols, said nonreactive compounds, and ethers;

(d) separating said First Ether Stream in a first separating zone under conditions that produce a Second Isoolefin/Alcohol Stream and a Second Ether Stream from said First Ether Stream, where said Second Isoolefin/Alcohol Stream comprises said unreacted isoolefins, said unreacted alcohols, and said nonreactive compounds, and said Second Ether Stream comprises said ethers, and where said Second Isoolefin/Alcohol Stream is lean in said ethers and said Second Ether Stream is rich in said ethers;

(e) contacting said Second Isoolefin/Alcohol Stream with a Third Water Stream in a third contacting zone under conditions that produce a First Alcohol/Water Stream and a Third Isoolefin Stream from said Second Isoolefin/Alcohol Stream and said Third Water Stream, where said Third Isoolefin Stream comprises said unreacted isoolefins and said nonreactive compounds, and where said First Alcohol/Water Stream comprises said unreacted alcohols and said water;

(f) separating said First Alcohol/Water Stream in a second separating zone where said First Alcohol/Water Stream is separated under conditions that produce said Third Water Stream and said First Alcohol Stream from said First Alcohol/Water Stream, where said First Alcohol Stream comprises said unreacted alcohols, and said Third Water Stream comprises water, and where said First Alcohol Stream is rich in said alcohols and said Third Water Stream is lean in said alcohols;

(g) contacting said Second Water Stream with a First Steam Stream in a fourth contacting zone under conditions that produce said First Water Stream and a First Nitrile Stream, from said Second Water Stream and said First Steam Stream where said First Water Stream comprises said water and said First Nitrile Stream comprises said nitriles, and where said First Water Stream is lean in said nitriles and said First Nitrile Stream is rich in said nitriles.

2. A process according to claim 1 wherein said isoolefin is selected from the group consisting of isobutylene, isoamylene, isohexylene, isoheptylene, isooctylene, isononylene, isodecylene, isoundecylene, isododecylene, isotridecylene, isotetradecylene, isopentadecylene, isohexadecylene and mixtures of two or more of said isoolefins.

3. A process according to claim 1 wherein said alcohol is selected from the group consisting of methanol, ethanol, propanol, isopropanol, butanol, secondary butanol, pentanol, hexanol, ethylene glycol, propylene glycol, butylene glycol, glycerol, and mixtures of two or more of said alcohols.

4. A process according to claim 1 wherein said isoolefin is selected from the group consisting of isobutylene and the isoamylenes and said alcohol is selected from the group consisting of methanol and ethanol.

5. A process according to claim 1 wherein said acidic-ion-exchange-resin catalyst is selected from the group consisting of sulfonated coals, sulfonated resins, and mixtures thereof.

6. A process according to claim 1 wherein said acidic-ion-exchange-resin catalyst is a sulfonated coal.

7. A process according to claim 1 wherein said acidic-ion-exchange-resin catalyst is a sulfonated resin.

8. A process according to claim 1 wherein said acidic-ion-exchange-resin catalyst is a sulfonated polystyrene resin.

9. An etherification process that resists deactivation, by nitriles, of its acidic-ion-exchange-resin catalyst, said process comprising:

(a) contacting a First Isoolefin Stream, which comprises isoolefins, nitriles, and nonreactive compounds, with a First Water Stream, which comprises water, in a first contacting means under conditions that produce a Second Isoolefin Stream and a Second Water Stream from said First Isoolefin Stream and said First Water Stream, where said Second Isoolefin Stream comprises said isoolefins and said nonreactive compounds, and where said Second Water Stream comprises said water and said nitriles, and where said Second Isoolefin Stream is lean in said nitriles when compared with said First Isoolefin Stream, and where said Second Water Stream is rich in said nitriles when compared with said First Water Stream;

(b) contacting said Second Isoolefin Stream with a First Alcohol Stream, which comprises alcohols, in an Isoolefin/Alcohol contacting zone where said Second Isoolefin Stream can come into contact with said First Alcohol Stream, to form a First Isoolefin/Alcohol Stream that comprises said isoolefins, said nonreactive compounds, and said alcohols;

(c) contacting said First Isoolefin/Alcohol Stream with an acidic-ion-exchange-resin catalyst, in a second contacting zone under conditions that produce a First Ether Stream from said First Isoolefin/Alcohol Stream, where said First Ether Stream comprises unreacted isoolefins, unreacted alcohols, said nonreactive compounds, and ethers;

(d) separating said First Ether Stream in a first separating zone under conditions that produce a Second Isoolefin/Alcohol Stream and a Second Ether Stream from said First Ether Stream, where said Second Isoolefin/Alcohol Stream comprises said unreacted isoolefins, said unreacted alcohols, and said nonreactive compounds, and said Second Ether Stream comprises said ethers, and where said Second Isoolefin/Alcohol Stream is lean in said ethers and said Second Ether Stream is rich in said ethers;

(e) contacting said Second Isoolefin/Alcohol Stream with a Third Water Stream in a third contacting zone under conditions that produce a First Alcohol/Water Stream and a Third Isoolefin Stream from said Second Isoolefin/Alcohol Stream and said Third Water Stream, where said Third Isoolefin Stream comprises said unreacted isoolefins and said nonreactive compounds, and where said First Alcohol/Water Stream comprises said unreacted alcohols and said water;

(f) separating said First Alcohol/Water Stream in a second separating zone where said First Alcohol/Water Stream is separated under conditions that produce said Third Water Stream and said First Alcohol Stream from said First Alcohol/Water Stream, where said First Alcohol Stream comprises said unreacted alcohols, and said Third Water Stream comprises water, and where said First Alcohol Stream is rich in said alcohols and said Third Water Stream is lean in said alcohols;

(g) contacting said Second Water Stream with a First Fuel Gas Stream in a fourth contacting zone under conditions that produce said First Water Stream and a First Nitrile Stream, from said Second Water Stream and said First Fuel Gas Stream where said First Water Stream comprises said water and said First Nitrile Stream comprises said nitriles, and where said First Water Stream is lean in said nitriles and said First Nitrile Stream is rich in said nitriles.

10. A process according to claim 9 wherein said isoolefin is selected from the group consisting of isobutylene, isoamylene, isohexylene, isoheptylene, isooctylene, isononylene, isodecylene, isoundecylene, isododecylene, isotridecylene, isotetradecylene, isopentadecylene, isohexadecylene and mixtures of two or more of said isoolefins.

11. A process according to claim 9 wherein said alcohol is selected from the group consisting of methanol, ethanol, propanol, isopropanol, butanol, secondary butanol, pentanol, hexanol, ethylene glycol, propylene glycol, butylene glycol, glycerol, and mixtures of two or more of said alcohols.

12. A process according to claim 9 wherein said isoolefin is selected from the group consisting of isobutylene and the isoamylenes and said alcohol is selected from the group consisting of methanol and ethanol.

13. A process according to claim 9 wherein said acidic-ion-exchange-resin catalyst is selected from the group consisting of sulfonated coals, sulfonated resins, and mixtures thereof.

14. A process according to claim 9 wherein said acidic-ion-exchange-resin catalyst is a sulfonated coal.

15. A process according to claim 9 wherein said acidic-ion-exchange-resin catalyst is a sulfonated resin.

16. A process according to claim 9 wherein said acidic-ion-exchange-resin catalyst is a sulfonated polystyrene resin.

17. A process comprising:

(a) contacting a First Isoolefin Stream, which comprises isoolefins, nitriles, and nonreactive compounds, with a First Water Stream, which comprises water, in a first contacting means under conditions that produce a Second Isoolefin Stream and a Second Water Stream from said First Isoolefin Stream and said First Water Stream, where said Second Isoolefin Stream comprises said isoolefins and said nonreactive compounds, and where said Second Water Stream comprises said water and said nitriles, and where said Second Isoolefin Stream is lean in said nitriles when compared with said First Isoolefin Stream, and where said Second Water Stream is rich in said nitriles when compared with said First Water Stream;

(b) contacting said Second Water Stream with a First Steam Stream, or a First Fuel Gas Stream, in a contacting zone under conditions that produce a First Nitrile Steam, from said Second Water Stream and said First Steam Stream, or said First Fuel Gas Stream, where said First Nitrile Stream comprises said nitriles.

* * * * *